United States Patent
Schlossman et al.

(10) Patent No.: US 11,357,716 B2
(45) Date of Patent: Jun. 14, 2022

(54) SUNSCREEN COMPOSITIONS

(71) Applicant: Kobo Products, Inc., South Plainfield, NJ (US)

(72) Inventors: David Schlossman, Short Hills, NJ (US); Yun Shao, Belle Mead, NJ (US); Luna Fascina, Valinhos (BR)

(73) Assignee: Kobo Products, Inc., South Plainfield, NJ (US)

( * ) Notice: Subject to any disclaimer, the term of this patent is extended or adjusted under 35 U.S.C. 154(b) by 0 days.

(21) Appl. No.: 16/305,951

(22) PCT Filed: Jun. 1, 2017

(86) PCT No.: PCT/US2017/035410
§ 371 (c)(1),
(2) Date: Nov. 30, 2018

(87) PCT Pub. No.: WO2017/210406
PCT Pub. Date: Dec. 7, 2017

(65) Prior Publication Data
US 2019/0183767 A1   Jun. 20, 2019

Related U.S. Application Data

(60) Provisional application No. 62/344,795, filed on Jun. 2, 2016.

(51) Int. Cl.
| | | |
|---|---|---|
| *A61K 8/49* | (2006.01) | |
| *A61K 8/27* | (2006.01) | |
| *A61K 8/25* | (2006.01) | |
| *A61Q 17/04* | (2006.01) | |
| *A61K 8/891* | (2006.01) | |

(52) U.S. Cl.
CPC .......... *A61K 8/4966* (2013.01); *A61K 8/25* (2013.01); *A61K 8/27* (2013.01); *A61K 8/891* (2013.01); *A61Q 17/04* (2013.01); *A61K 2800/412* (2013.01)

(58) Field of Classification Search
CPC ......... A61K 8/4966; A61K 8/27; A61Q 17/04
See application file for complete search history.

(56) References Cited

U.S. PATENT DOCUMENTS

| | | | |
|---|---|---|---|
| 2005/0136012 A1 | 6/2005 | Gonzalez et al. | |
| 2010/0092411 A1* | 4/2010 | Katusic | B82Y 30/00 424/59 |
| 2010/0119464 A1 | 5/2010 | Gaudry et al. | |
| 2012/0107253 A1* | 5/2012 | Xing | A61Q 17/04 424/59 |
| 2013/0095151 A1* | 4/2013 | Jawale | A61K 8/35 424/400 |
| 2013/0118517 A1* | 5/2013 | Foley | A61K 8/042 132/200 |
| 2013/0336908 A1 | 12/2013 | Yamaguchi et al. | |
| 2014/0170093 A1 | 6/2014 | Halpern et al. | |
| 2015/0147632 A1 | 5/2015 | Wang et al. | |
| 2015/0202145 A1 | 7/2015 | Friedman | |

FOREIGN PATENT DOCUMENTS

| | | |
|---|---|---|
| CN | 102596160 A | 7/2012 |
| EP | 2185126 A2 | 5/2010 |
| JP | 2007503373 A | 2/2007 |
| JP | 2014240382 A | 12/2014 |
| JP | 2015044879 A | 3/2015 |
| WO | 2003039507 A1 | 5/2003 |
| WO | 2004069216 A1 | 8/2004 |
| WO | 2007128840 A2 | 11/2007 |
| WO | 2013173336 A1 | 11/2013 |

OTHER PUBLICATIONS

Love sun buddy, Dec. 15, 2012, https://lovesunbody.com/pages/truly-effective-sunscreens, 5 pages (Year: 2012).*

Hong et al., "A comparative study of the physical and chemical properties of nano-sized ZnO particles from multiple batches of three commercial products," Journal of Nanoparticle Research (Feb. 17, 2015); 17(2):1-19.

\* cited by examiner

*Primary Examiner* — Kyle A Purdy
(74) *Attorney, Agent, or Firm* — Fox Rothschild LLP

(57) ABSTRACT

Sunscreen compositions containing bis-ethylhexyloxyphenol methoxyphenyl triazine (BEMT) and zinc oxide, especially non-nano zinc oxide materials, with synergistic effects on enhancing in vivo sun protection factor (SPF) and UVA protection factor (PFA) values, and methods of preparation and applications thereof are disclosed.

21 Claims, No Drawings

SUNSCREEN COMPOSITIONS

CROSS-REFERENCE TO RELATED APPLICATION

This application is the U.S. National Phase of International Patent Application No. PCT/US2017/035410, filed Jun. 1, 2017, which claims priority under 35 U.S.C. § 109(e) to U.S. Provisional Application Ser. No. 62/344,795, filed Jun. 2, 2016, the disclosures of both of which are incorporated herein by reference in their entirety.

FIELD OF THE INVENTION

The present invention is in the technical field of cosmetic sunscreen compositions and raw material applications, in particular relating to broad-spectrum sunscreen compositions containing bis-ethylhexyloxyphenol methoxyphenyl triazine (BEMT) and non-nano zinc oxide.

BACKGROUND OF THE INVENTION

Solar radiation includes about 5% ultraviolet (UV) radiation, with wavelength in the range of 200 nm to 400 nm, which can be classified into three regions: from 320 to 400 nm (UV-A), from 290 to 320 nm (UV-B), and from 200 to 290 nm (UV-C). Most UVC is absorbed by the ozone layer and does not reach the earth, but both UVA and UVB can penetrate the atmosphere. It was once thought that only UVB was of concern, but with increasing studies conducted and knowledge gained about the damages that can be caused by UVA on human body, it has been realized that both UVA and UVB can cause various health-related issues. Exposure to UV-A and UV-B radiation for short periods can cause reddening and irritation of the skin, and prolonged exposure can lead to sunburn, premature skin aging, hair damage, eye damage (including cataracts), and melanoma and other skin cancers. Therefore, protection from too much UV-A and UV-B radiation is an important part of personal care.

While many UV-B sunscreens are known and approved for safe use in the protection from UV radiation, search for new ways to protect from UVA radiation has emerged to be an important endeavor in this field, with a goal to develop broad-spectrum sun care product that can protect from both UV-A and UV-B radiations. Sun protection Factor (SPF) and Protection factor in UVA (PFA) are commonly measured attributes of photoprotective compositions, which indicate the respective protection that the skin gets from exposure to both UV-B and UV-A radiations.

Zinc oxide is a globally approved sunscreen active ingredient and has been widely used in sun care formulations because it is inert and does not cause allergy or sting to consumers with sensitive skin. Zinc oxide has been approved to be a UVA sunscreen ingredient mainly owing to its UVA absorption. Study has shown that micro ZnO can provide satisfactory UVA protection as indicated by PFA values measured by in vivo persistent pigment darkening method; however, ZnO can provide only weak UVB protection (D. Schlossman and Y. Shao, "Inorganic Ultraviolet Filters" in *Sunscreens: Regulations and Commercial Development*, 3$^{rd}$ Ed. by N Shaath, Taylor & Francis, March 2005). In particular, when the primary size of ZnO becomes large, such as in non-nano range (D50>100 nm), its protective effect in both UVA and UVB regions becomes less effective than the nano-ZnO counterpart. Therefore, to meet the performance requirement of SPF 30 or higher with a broad-spectrum protection, ZnO is often used along with other organic sunscreens and/or titanium dioxide.

Bis-ethylhexyloxyphenol methoxyphenyl triazine (BEMT) under the trade name of Tinosorb® S is made by BASF (formerly Ciba) for UVA protection in sunscreen formulations. However, in a study by BASF scientists (Uli Osterwalder, et al., *How to Fulfill the new UVA Protection Standards*, In-Cosmetics, Paris, 17-19 Apr. 2007), the performance of the BEMT was shown to be unremarkable, as follows:

| Active: | BEMT 4% |
|---|---|
| SPF | in vivo = 7.3 ± 1.2 |
| UVA-PF | in vivo = 7.6 ± 2.2 |

Therefore, in spite of the fact that both BEMT and zinc oxide have been used as sunscreen active ingredients in sun care products, how to make best use of these two generally useful sunscreen ingredients into useful formulations remains to be a challenge, especially when the size of ZnO is large.

SUMMARY OF THE INVENTION

The present invention is based upon a surprising discovery of the synergies between BEMT and non-nano ZnO in protection against both UVA and UVB radiations. Where the use level of BEMT is not more than 2% by weight, the combination provides a broad-spectrum and high UV protection. In particular, the present invention provides the use of BEMT with non-nano ZnO with a median primary particle size above 100 nm, with a level of non-nano ZnO up to 25% by weight.

Thus, in one aspect, the present invention provides a sunscreen composition comprising non-nano ZnO and bis-ethylhexyloxyphenol methoxyphenyl triazine, and optionally another organic or inorganic UV filter.

In another aspect, the present composition provides a cosmetic or personal care formulation comprising a sunscreen composition according to any embodiments, or combinations thereof, as disclosed herein.

In another aspect, the present composition provides an article comprising a sunscreen composition according to any embodiments, or combinations thereof, as disclosed herein.

Other aspects or benefits of the present invention will be better appreciated in the following detailed description and claims.

DETAILED DESCRIPTION OF THE INVENTION

In contrast to the conventional belief that ZnO in large particle sizes usually provides less effective UV protection, it has been discovered that synergies exist when non-nano ZnO is combined with BMET. The sunscreen composition of present invention contains ZnO, especially non-nano ZnO with median primary particle over 100 nm, and BEMT.

A high synergy between ZnO and BEMT was discovered surprisingly when non-nano ZnO is used at a level up to 25 wt % and BEMT up to 2 wt %. According to the performance data reported in the above-mentioned literature, the calculated SPF and PFA are expected to be only lower than 15 and lower than 8, respectively. A sunscreen product with such a SPF would be required to bear the warning label on the package, thus affecting its marketability. In sharp contrast, the combination of non-nano ZnO and BEMT of the present invention was tested to have SPF and PFA values higher than 35 and higher than 25, respectively.

Thus, in one aspect, the present invention is directed to applying a combination of ZnO and BEMT to making sunscreen compositions.

In one aspect, the present invention provides a sunscreen composition comprising non-nano ZnO and BEMT in a ratio at which a synergistic effect is obtained in UV protection.

In one embodiment, the synergistic effect is represented by an increased sun protection factor (SPF) value, an increased UVA protection factor (PFA) value, or both, as measured in vivo, in comparison with the corresponding mathematically calculated SPF and/or PFA value(s) based on the values of the two individual components.

In some embodiments, the increased SPF value is at least 15, at least 16, at least 18, at least 20. In some embodiments, the SPF value is at least 25, at least 30, or at least 35.

In some embodiments, the increased PFA value is at least 8, least 10, at least 12, or at least 15. In some embodiments, the PFA value is at least 18, at least 20, at least 22, or at least 24.

A person skilled in the art would be able to adjust the amounts and ratio of non-nano ZnO and BMET to achieve a desired combination of SPF and PFA values based on the present disclosure.

In one embodiment, the ZnO has a median primary particle size in the range of about 20-300 nm.

In another embodiment, the ZnO has a median primary particle size in the range of about 20-100 nm.

In another embodiment, the ZnO has a median primary particle size of about 100 nm or higher ("non-nano ZnO").

In another embodiment, the ZnO has a median primary particle size in the range of about 100-300 nm.

In another embodiment, the ZnO has a median primary particle size in the range of about 100-200 nm.

In another embodiment, the ZnO has a median primary particle size in the range of about 200-300 nm.

In one embodiment, the ZnO is not coated.

In another embodiment, the ZnO is coated with a different oxide compound.

In another embodiment, said different oxide compound is silica.

In another embodiment, the ZnO is additionally coated with an organic material selected from the group consisting of silanes, silicones, organic titanates, fatty acids, metal soaps, polyols, dimethicones, and combinations thereof.

In another embodiment, the ZnO content is at a level up to about 25% by weight.

In another embodiment, the ZnO content is at a level in the range of about 0.1% to about 25% by weight.

In another embodiment, the ZnO content is at a level in the range of about 1% to about 20% by weight.

In another embodiment, the ZnO content is at a level in the range of about 2% to about 15% by weight.

In another embodiment, the ZnO content is at a level in the range of about 3% to about 10% by weight.

In another embodiment, bis-ethylhexyloxyphenol methoxyphenyl triazine (BEMT) content is at a level up to about 2% by weight.

In another embodiment, the BEMT content is at a level in the range of about 0.1% to about 2% by weight.

In another embodiment, the BEMT content is at a level in the range of about 0.2% to about 1.8% by weight.

In another embodiment, the BEMT content is at a level in the range of about 0.3% to about 1.6% by weight.

In another embodiment, the BEMT content is at a level in the range of about 0.5% to about 1.5% by weight.

In another embodiment, the sunscreen composition is unpigmented for skin, hair or nail care.

In another embodiment, the sunscreen composition is a color cosmetic selected from the group consisting of foundation, lipstick, nail polish, and pressed powder, or the like.

In another embodiment, the sunscreen composition further comprises an additional organic or inorganic UV filter.

In some embodiments, the sunscreen composition further comprises a topically active agent selected from the group consisting of a sunless tanning agent, an antimicrobial agent, a depigmentation agent, an anti-aging agent, an antifungal agent, an insect repellent, and a combination thereof.

In another aspect, the present invention provides sunscreen compositions as substantially described and shown, particularly in one embodiment, as described in Table 1.

In another aspect, the present composition provides a cosmetic or personal care formulation comprising a sunscreen composition according to any embodiments, or combinations thereof, as disclosed herein.

In another aspect, the present composition provides an article comprising a sunscreen composition according to any embodiments, or combinations thereof, as disclosed herein. The article may be in the form of a container of the sunscreen composition, including, but not limited to, tubes, bottles, cases, boxes, bags, spraying devices, or the like, which can be in any shape, style, or color, and can be made in any materials suitable for containing the sunscreen composition.

In another aspect, the present composition provides applications of a sunscreen composition according to any embodiments, or combinations thereof, as disclosed herein.

In another aspect, the present invention provides a composition of the first aspect of the invention for obtaining SPF higher than 15. The SPF is preferably higher than 20, more preferably higher than 25, and further more preferably higher than 30. The composition as prepared in Table 1 of Example provided a high SPF value of 38.

The invention thus provides for a high SPF sunscreen composition comprising relatively low amount of sunscreen compounds and low cost materials, thus achieving the overall benefits at a low cost.

The sunscreen formulations of the present invention can contain one or more other organic or inorganic UV filters so long as the synergy between the non-nano ZnO and BEMT is retained, as a person of ordinary skill in the art would appreciate.

Inorganic UV filters can include, but are not limited to, titanium dioxide ($TiO_2$), iron oxides (e.g., $Fe_2O_3$), and silica, or the like.

Numerous organic UV filters have been reported in the field of cosmetics, which include, but are not limited to, benzophenones, e.g., benzophenone-3 (BP3) and benzophenone-4 (BP4); salicylates, e.g., homosalate (HMS), 2-ethylhexyl salicylate (EHS); p-aminobenzoic acid (PABA) and derivatives, e.g., ethylhexyl dimethyl PABA (OD-PABA), 4-p-aminobenzoic acid (PABA); benzimidazole derivatives, e.g., phenylbenzimidazole sulfonic acid (PMDSA), disodium phenyl dibenzimidazole tetrasulfonate (bisdisulizole disodium); triazines, e.g., ethylhexyltriazone (OT), diethylhexyl butamido triazone (DBT), benzotriazoles, drometrizole trisiloxane (DRT), methylene bis-benzotriazolyl tetramethylbutylpheno (biscotrizole) (MBP); dibenzoyl methane derivatives, e.g., butyl methoxydibenzoyl methane (BM-DBM); cinnamates, e.g., ethylhexyl methoxycinnamate (OMC), isoamyl p-methoxycinnamate (IMC); and camphor derivatives, e.g., terephthalyidene dicamphor sulfonic acid (PDSA), 3-benzylidene camphor (3BC), benzylidene camphor sulfonic acid (BCSA), 4-methylbenzylidene camphor (4-MBC), polyacrylamidomethyl benzylidene camphor (PBC), and camphor benzalkonium methosulfate (CBM).

Among the organic UV filters are existed a particularly useful dibenzoylmethane class of compounds, which include, but are not limited to, 4-tert-butyl-4'-methoxydibenzoylmethane, 2-methyldibenzoylmethane, 4-methyl-dibenzoyl-ethane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoyl-methane, 2-methyl-5-isopropyl-4'-methoxydibenzoylmethane, 2-methyl-5-tert-butyl-4'-methoxy-dibenzoyl methane, 2,4-dimethyl-4'-methoxy dibenzoylmethane, 2,6-dimethyl-4-tert-butyl-4'-methoxy-dibenzoylmethane, or the like.

All the above organic UV filters or the like may be used in the present invention to further enhance or adjust the desired UV protection effect.

The sunscreen formulations can also include various other ingredients, for example, cosmetically acceptable bases, surfactants, diluents, and various other optional ingredients, etc., as generally known by a person skilled in the art and accepted by the personal care and cosmetics industries. See, e.g., WO 96/41614, US 2013/0266527, and U.S. Pat. No. 9,649,263, all of which are herein incorporated by reference in their entireties.

In some preferred embodiments, the sunscreen formulations of the present invention contain the components listed in Table 1, or their functional equivalents and/or variants.

While not being intended to be limiting, the sunscreen formulations of the present invention can be prepared preferably in the form of cream, lotion, gel or emulsion, depending on the bases used. A preferred solid form of the composition is cream or lotion. Creams are typically defined as those compositions that do not flow out from a container at 25° C. when it is turned upside down; whereas lotions are those compositions that flow out from the container at 25° C. when turned upside down (See, e.g., Brummer, R.; *Rheology Essentials of Cosmetic and Food Emulsions*, Springer-Verlag Berline Heidelberg, 81-83 (2006)).

The sunscreen compositions of the present invention can contain a wide range of other optional components, for example, antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, skin healing agents, or the like. See, e.g., *The CTFA Cosmetic Ingredient Handbook*, Second Edition, 1992, which describes a wide variety of non-limiting cosmetic and pharmaceutical ingredients commonly used in the skin care industry, which are suitable for use in the compositions of the present invention.

The term "non-nano ZnO", as used herein, means that a median primary particle size of the ZnO is larger than 100 nm. Particle size is calculated by measuring the particles in photographs obtained using transmission electron microscopy or scanning electron microscopy. Number weighted distribution of the shortest dimension, when applicable, is used for size analysis and for discussion in this application.

The term "about," as used herein, means that a number can vary up to ±20%, preferably within ±10%, and more preferably within ±5%. When "about" is used in front of a range, it applies to both upper and lower limits of the range.

The term "a," "an," or "the," as used herein, represents both singular and plural forms. In general, when either a singular or a plural form of a noun is used, it denotes both singular and plural forms of the noun.

The following non-limiting example further illustrates certain aspects of the present invention.

EXAMPLE

Surprisingly, the exemplified formula in Table 1 containing 7.15% of a non-nano ZnO and 1.4% of BEMT as tested in-vivo showed a SPF of 38.89 (Table 2), a PFA of 25.27 and a critical wavelength of 377 nm (Table 3). Such a sunscreen formulation has a high SPF 30+, i.e., a broad spectrum UV protection according to both FDA and Cosmetic Europe regulations, and a ++++ UVA protection rating according to Japanese regulation.

TABLE 1

Example Sunscreen Formula

| Part | Percent | KOBO_Name | INCI Name |
|---|---|---|---|
| 1 | 53.00 | Deionized Water | Water |
| 2 | 1.00 | Liposorb ® L-20 | Polysorbate 20 |
|   | 0.20 | Methyl Paraben NF | Methylparaben |
| 3 | 4.00 | GLICERINA | Glycerin |
|   | 0.20 | GOMA XANTANA | Xanthan Gum |
| 4 | 23.15 | Tegosoft ® TN | C12-15 Alkyl Benzoate |
|   | 9.10 | TNPB80MZCM-G | Zinc Oxide (And) C12-15 Alkyl Benzoate (And) Isopropyl Myristate (And) Polyhydroxystearic Acid (And) Stearalkonium Hectorite (And) Hydrogen Dimethicone (And) Glyceryl Behenate/Eicosadioate (And) Propylene Carbonate |
|   | 2.45 | Lipopeg ® 100-S | PEG-100 Stearate |
|   | 1.40 | Tinosorb ® S | Bis-Ethylhexyloxyphenol Methoxyphenyl Triazine |
|   | 1.00 | TEGIN ® M Pellets | Glyceryl Stearate |
|   | 0.40 | SALACOS ® 334 | Caprylic/Capric/Myristic/Stearic Triglyceride |
|   | 0.10 | Propyl Paraben NF | Propylparaben |
| 5 | 3.00 | MSS-500W | Silica |
|   | 1.00 | Sepigel ™ 305 | Polyacrylamide (And) C13-14 Isoparaffin (And) Laureth-7 |

Actives: BEMT: 1.4%; ZnO: 7.15%
Procedure:
1. Combined Parts 1 and 2 and heated to 80° C.
2. Combined Part 3 ingredients into a slurry and added to Parts 1 and 2 while mixing.
3. Combined ingredients of Part 4 and heated to 80° C.
4. Combined the mixture of Parts 1-3 with that of Part 4 under homogenization.
5. Cooled to 50° C. and added Part 5 into the mixture of Parts 1-4.
Summary of Test Results:

TABLE 2

SPF Test Results

| Volunteers | | | product Reference (P2) | | | Product-Test | |
|---|---|---|---|---|---|---|---|
| Entry | Skin type | ITA° | MDEn | MDEp | FPSi | MDEp | SPF individual |
| 1 | III | 46 | 1.41 | 20.51 | 14.55 | 55.18 | 39.13 |
| 2 | III | 49 | 1.68 | 25.66 | 15.27 | 65.21 | 38.82 |

TABLE 2-continued

SPF Test Results

| Volunteers | | | product Reference (P2) | | | Product-Test | |
|---|---|---|---|---|---|---|---|
| Entry | Skin type | ITA° | MDEn | MDEp | FPSi | MDEp | SPF individual |
| 3 | III | 49 | 1.68 | 24.89 | 14.82 | 65.33 | 38.89 |
| Mean | | | | | | | 38.89 |

TABLE 3

PFA Test Results (by PPD method)

| Entry | Skin type | DPM unprotected skin (Joules) | DPM Protected skin (Joules) | PFA individual |
|---|---|---|---|---|
| 1 | III | 17.4 | 400.20 | 23.00 |
| 2 | III | 17.2 | 472.31 | 27.46 |
| 3 | III | 21.6 | 560.74 | 25.96 |
| Mean | | | | 25.47 |

The foregoing examples or preferred embodiments are provided for illustration purpose and are not intended to limit the present invention. Numerous variations and combinations of the features set forth above can be utilized without departing from the present invention as set forth in the claims. All references cited are incorporated herein by reference in their entirety for all purposes.

What is claimed is:

1. A sunscreen composition for broad spectrum protection against solar radiation, consisting of 1-25 percent of an inorganic sunscreen active by weight, 0.1-2 percent of an organic sunscreen active by weight, and one or more cosmetic or personal care ingredients, wherein the inorganic and organic sunscreen actives are non-nano zinc oxide and bis-ethylhexyloxyphenol methoxyphenyl triazine (BEMT), respectively; and wherein the SPF value of the composition is at least 25, and the PFA value of the composition is at least 15.

2. The sunscreen composition of claim 1, wherein the zinc oxide has a median primary particle size of 100-300 nm.

3. The sunscreen composition of claim 1, wherein the zinc oxide has a median primary particle size of 100-200 nm.

4. The sunscreen composition of claim 1, wherein the zinc oxide has a median primary particle size of 200-300 nm.

5. The sunscreen composition of claim 1, wherein the sunscreen composition has a sun protection factor (SPF) greater than 35, a UV-A protection factor (PFA) greater than 25, and a critical wavelength (CW) greater than 375 nm.

6. The sunscreen composition of claim 2, wherein the sunscreen composition has a sun protection factor (SPF) greater than 35, a UV-A protection factor (PFA) greater than 25, and a critical wavelength (CW) greater than 375 nm.

7. The sunscreen composition of claim 4, wherein the sunscreen composition has a sun protection factor (SPF) greater than 35, a UV-A protection factor (PFA) greater than 25, and a critical wavelength (CW) greater than 375 nm.

8. The sunscreen composition of claim 1, wherein the zinc oxide is coated with an organic material selected from the group consisting of silanes, silicones, organic titanates, fatty acids, metal soaps, polyols, dimethicones, and combinations thereof.

9. The sunscreen composition of claim 6, wherein the zinc oxide is coated with an organic material selected from the group consisting of silanes, silicones, organic titanates, fatty acids, metal soaps, polyols, dimethicones, and combinations thereof.

10. The sunscreen composition of claim 7, wherein the zinc oxide is coated with an organic material selected from the group consisting of silanes, silicones, organic titanates, fatty acids, metal soaps, polyols, dimethicones, and combinations thereof.

11. The sunscreen composition of claim 2, wherein the zinc oxide content is 1-20 percent by weight.

12. The sunscreen composition of claim 2, wherein the zinc oxide content is 2-15 percent by weight.

13. The sunscreen composition of claim 2, wherein the zinc oxide content is 3-10 percent by weight.

14. The sunscreen composition of claim 4, wherein the zinc oxide content is 1-20 percent by weight.

15. The sunscreen composition of claim 4, wherein the zinc oxide content is 2-15 percent by weight.

16. The sunscreen composition of claim 4, wherein the zinc oxide content is 3-10 percent by weight.

17. The sunscreen composition of claim 1, wherein the zinc oxide is provided as an oil dispersion.

18. The sunscreen composition of claim 1, wherein the zinc oxide content is 2-15 percent by weight; the zinc oxide has a median primary particle size of 100-300 nm; the BEMT content is 1-1.8 percent by weight; and the sunscreen composition has a sun protection factor (SPF) greater than 35 and a UV-A protection factor (PFA) greater than 25.

19. An sunscreen composition, comprising between about 1% and about 25% of non-nano ZnO by weight, between about 0.1% and about 2% of bis-ethylhexyloxyphenol methoxyphenyl triazine (BEMT) by weight, polysorbate 20, methylparaben and/or propylparaben, glycerin, xanthan gum, $C_{12-15}$ alkyl benzoate, isopropyl myristate, polyhydroxystearic acid, stearalkonium hectorite, hydrogen dimethicone, glyceryl behenate/eicosadioate, propylene carbonate, PEG-100 stearate, glyceryl stearate, silica, polyacrylamide, $C_{13-14}$ isoparaffin, laureth-7, and caprylic, capric, myristic, and/or stearic triglyceride, wherein the SPF value of the composition is at least 25, and the PFA value of the composition is at least 15.

20. A sunscreen composition, comprising non-nano zinc oxide (ZnO), bis-ethylhexyloxyphenol methoxyphenyl triazine (BEMT), polysorbate 20, methylparaben and/or propylparaben, glycerin, xanthan gum, $C_{12-15}$ alkyl benzoate, isopropyl myristate, polyhydroxystearic acid, stearalkonium hectorite, hydrogen dimethicone, glyceryl behenate/eicosadioate, propylene carbonate, PEG-100 stearate, glyceryl stearate, caprylic, capric, myristic, and/or stearic triglyceride, silica, polyacrylamide, $C_{13-14}$ isoparaffin, and laureth-7, wherein the non-nano ZnO and BEMT are present in a weight ratio at which the sunscreen composition has an increased sun protection factor (SPF) value, and an increased UVA protection factor (PFA) value, as compared to the corresponding mathematically calculated SPF and PFA values.

21. A sunscreen composition for broad spectrum protection against solar radiation, consisting of 1-25 percent of an inorganic sunscreen active by weight, 0.1-2 percent of an organic sunscreen active by weight, and one or more cosmetic or personal care ingredients, wherein the inorganic and organic sunscreen actives are non-nano zinc oxide and bis-ethylhexyloxyphenol methoxyphenyl triazine (BEMT), respectively; wherein the SPF value of the composition is at least 25, and the PFA value of the composition is at least 15; and wherein the critical wavelength of the composition is greater than 370 nm.

\* \* \* \* \*